(12) United States Patent
Kitamura et al.

(10) Patent No.: US 6,265,574 B1
(45) Date of Patent: Jul. 24, 2001

(54) PROCESS FOR PRODUCING ε-CAPROLACTAM

(75) Inventors: Masaru Kitamura; Yasumoto Shimazu, both of Niihama; Makoto Yako, Takatsuki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/500,997

(22) Filed: Feb. 9, 2000

(30) Foreign Application Priority Data

Feb. 9, 1999 (JP) .................................................. 11-031226

(51) Int. Cl.⁷ ................................................ C07D 201/04
(52) U.S. Cl. ............................................................ 540/536
(58) Field of Search ............................................... 540/536

(56) References Cited

U.S. PATENT DOCUMENTS

| | | | |
|---|---|---|---|
| 4,155,876 | 5/1979 | Danziger et al. | 252/417 |
| 4,248,782 | 2/1981 | Fuchs et al. | 260/239.3 A |
| 5,071,802 | * 12/1991 | Shimizu et al. | 502/38 |
| 5,741,904 | 4/1998 | Hoelderich et al. | 540/536 |

FOREIGN PATENT DOCUMENTS

| | | |
|---|---|---|
| 19608660A | 11/1996 | (DE) . |
| 0388070A1 | 9/1990 | (EP) . |
| 0544531A1 | 6/1993 | (EP) . |
| 1535700 | 12/1978 | (GB) . |

* cited by examiner

*Primary Examiner*—Bruck Kifle
(74) *Attorney, Agent, or Firm*—Birch, Stewart Kolasch & Birch, LLP

(57) ABSTRACT

A process for producing ε-caprolactam is provided which comprises the steps of subjecting cyclohexanone oxime to a gaseous phase Beckmann rearrangement reaction in a fluidized bed system using a solid catalyst and re-generating the catalyst, wherein said process comprises a step of treating the catalyst with an oxygen-containing gas at an elevated temperature in a re-generation step so that the nitrogen content of the catalyst falls within a range of 10 ppm to 2,500 ppm on its way to the reaction step from the re-generating step. According to the present invention, ε-caprolactam is produced with a high conversion or a high selectivity without interrupting the rearrangement reaction or the re-generation step.

6 Claims, 1 Drawing Sheet

PROCESS FOR PRODUCING ε-CAPROLACTAM

BACKGROUND OF THE INVENTION

1. Field of the Invention

The present invention relates to an improved process for producing ε-caprolactam which comprises subjecting cyclohexanone oxime to Beckmann rearrangement under gaseous phase reaction conditions in a fluidized bed reaction using a solid catalyst, wherein a fluidized bed reaction system with a re-generator for the catalyst is used.

2. Description of Related Art

ε-Caprolactam is a key chemical product used as a raw material for Nylon or the like. Among processes for its production, a process that has conventionally been adopted in the industrial production thereof is a process in which cyclohexanone oxime is subjected to Beckmann rearrangement with fuming sulfuric acid under liquid phase conditions.

In addition, many variations for its production have been proposed in which cyclohexanone oxime is subjected to Beckmann rearrangement with a solid acid as the catalyst under gaseous phase reaction conditions (gaseous phase Beckmann rearrangement). For example, processes are known using a boric acid catalyst (JP-A-53-37686, JP-A-46-12125), a silica-alumina catalyst (British Patent No. 881,927), a solid phosphoric acid catalyst (British Patent No. 881,956), a Y-type zeolite catalyst (Journal of Catalysis, 6, 247 (1966)), a crystalline aluminosilicate catalyst (JP-A-57-139062) or the like.

Furthermore, a process has been proposed in which a lower alcohol coexists in the reaction system (JP-A-2-275850).

As the reaction methodology, a method has been proposed in which cyclohexanone oxime is subjected to rearrangement in a fluidized bed using a boric acid catalyst on a carrier under gaseous phase conditions, an oxygen-containing gas is concurrently utilized to re-generate the catalyst in the fluidized bed, and boron trioxide or boric acid is added to the catalyst in fluidized state before the catalyst is returned to the reactor for the rearrangement (JP-A-55-53267).

Yet further, in carrying out gaseous phase Beckmann rearrangement with a boric acid catalyst carried on carbon in a fluidized bed system, the difference between the organic nitrogen content of the catalyst in a reactor and that of the catalyst in a re-generator is maintained within a certain range when the catalyst is withdrawn from the reactor of the fluidized bed to re-generate and returned upon re-generation to the bed (JP-A-53-35691). In this case, it is known that a scattering of a part of boric acid as a component of the catalyst is unavoidable in the re-generation step, and almost the same amount of carrier carbon for the catalyst as that of the scattering boric acid is lost by burning.

The above-described conventional Beckmann rearrangement process using fuming sulfuric acid, which has been widely adopted in the industry, had not only a problem in that a large amount of fuming sulfuric acid is required but also a problem in that neutralization of sulfuric acid with ammonia is necessary for recovering ε-caprolactam from the reaction product of Beckmann rearrangement. In this step, as much as about 1.5 ton of ammonium sulfate per ton ε-caprolactam is produced as the by-product.

On the other hand, the gaseous phase Beckmann rearrangement process using a solid catalyst has an advantage that no ammonium sulfate is produced in the step of the Beckmann rearrangement thereof. Various catalysts suitable for the gaseous phase Beckmann rearrangement have been proposed. All the catalysts have a problem that carbonaceous substances deposit on the catalyst during the reaction, resulting in coverage of active sites by the carbonaceous substances, which leads to gradual deactivation of the catalyst. Recovery of the catalytic activity is possible by interrupting the reaction at an appropriate time, sending an oxygen-containing gas to the catalyst bed and removing the carbonaceous substances by oxidation. However, this raises another problem that the production of ε-caprolactam is interrupted during the regeneration operation for the catalyst in the case of the fixed bed reaction system, and a switching operation between the reaction and the re-generation is troublesome. A method is also known in which both a step of gaseous phase Beckmann rearrangement reaction and a re-generation reaction step for the catalyst are performed in a fluidized bed system, and both the rearrangement reaction and the re-generation are continuously carried out by circulating the catalyst through a reactor and a re-generator. In this case, there is a problem that it is difficult to maintain a high conversion or a high selectivity in the Beckmann rearrangement reaction and to continue a stable production for a long term and, therefore, an improved process which solves such a problem has been demanded.

SUMMARY AND OBJECTS OF THE INVENTION

In view of the above circumstances, the present inventors have made extensive studies with the object of providing a process for producing ε-caprolactam maintaining a high conversion or a high selectivity while continuously carrying out the gaseous phase Beckmann rearrangement and the operation for the re-generation of a catalyst.

As a result, the present inventors have found that the production of ε-caprolactam maintaining a high conversion or a high selectivity can be attained without interrupting the production by carrying out both a step of gaseous phase Beckmann rearrangement reaction and a re-generation step for the catalyst in a fluidized bed system, circulating the catalyst between the step of Beckmann rearrangement and the regeneration step for the catalyst, and controlling the nitrogen content of the catalyst returning from the re-generation step to the step of Beckmann rearrangement within a specific range. The present invention has been accomplished on the basis of the above findings.

Thus, the present invention provides a process for producing ε-caprolactam which comprises the steps of (i) subjecting cyclohexanone oxime to a gaseous phase Beckmann rearrangement reaction in a fluidized bed system using a solid catalyst, excluding a boric acid catalyst, and (ii) regenerating the said catalyst for use in step (i), wherein said step of re-generating the said catalyst comprises the substeps of (a) continuously or intermittently withdrawing the catalyst from the Beckmann rearrangement reaction step (i), (b) treating the catalyst with an oxygen-containing gas at an elevated temperature so that the nitrogen content of the catalyst falls within a range of from 10 ppm to 2,500 ppm on its way to the reaction step from the re-generating step, and (c) returning the so treated catalyst to the Beckmann rearrangement reaction step (i).

DETAILED DESCRIPTION OF THE INVENTION

Figure 1:
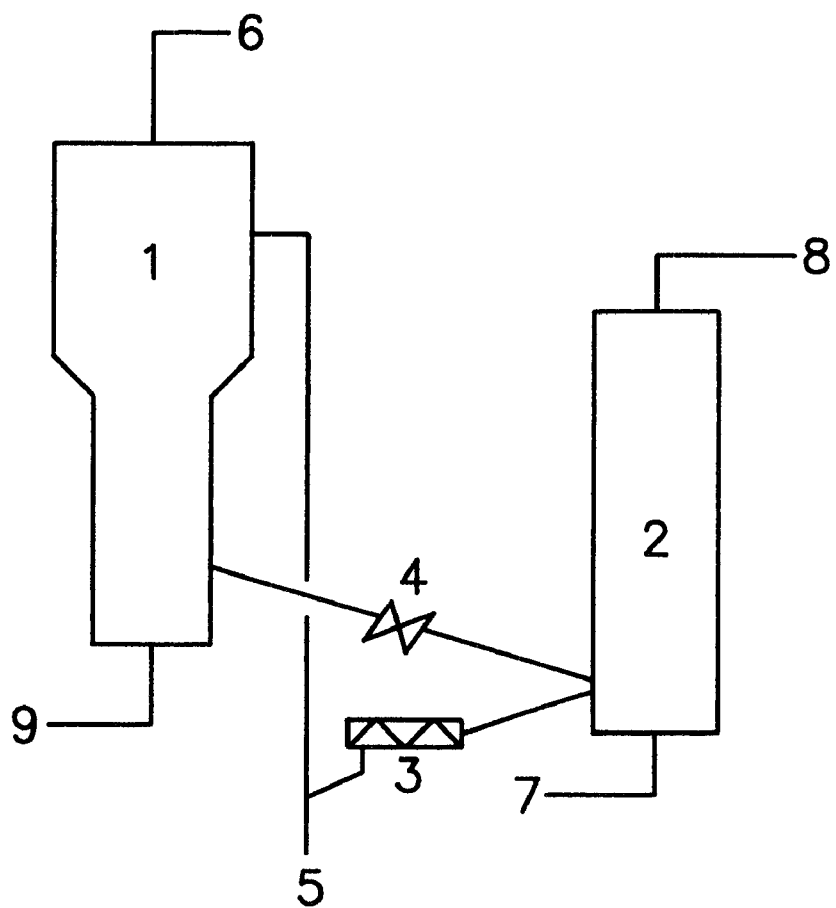
FIG. 1 is a schematic view of an apparatus used in the present invention showing a Beckmann rearrangement step and a re-generation step for the catalyst, wherein 1 denotes a reactor, 2 a re-generator, 3 a screw feeder, 4 a control valve and 5 to 9 each a pipe.

A process for producing ε-caprolactam of the present invention comprises the steps of subjecting cyclohexanone oxime to a gaseous phase Beckmann rearrangement reaction in a fluidized bed system using a solid catalyst and re-generating the catalyst.

Examples of the solid catalyst used in the present invention include a zeolite catalyst and exclude a boric acid catalyst. A pentasil-type zeolite is preferably used. Among the pentasil-type zeolite, particularly preferred is a zeolite with a MFI structure. The element component constituting the skeleton of zeolite may contain silicon as its principal component and another component element M, wherein M is one or more members selected from Al, B, Ga, In, Ge, Fe, Ti and Zr. The atomic ratio Si/M is 50 or more, preferably 500 or more. A zeolite having a skeleton of $SiO_4$ tetrahedron substantially consisting of silicon and oxygen may be utilized.

In the present invention, both the Beckmann rearrangement step and the re-generation step are carried out in a fluidized bed system. One of the embodiments of the present invention is illustrated in FIG. 1. In FIG. 1, a vapor of cyclohexanone oxime is fed into a reactor 1 for Beckmann rearrangement packed with a zeolite catalyst through a pipe 9. The reaction product containing ε-caprolactam as its principal component is withdrawn in a gaseous state towards the outside of the system through a pipe 6. A part of the catalyst is withdrawn continuously or intermittently from the reactor 1 by a control valve 4 and is sent to a re-generator 2 for the catalyst in a fluidized bed system. In the regenerator 2, the catalyst is treated with an oxygen-containing gas introduced from a pipe 7. As the result, carbonaceous substances deposited on the catalyst are removed, for example, by a reaction with oxygen or by evaporation at a high temperature. The extent of removal of the carbonaceous substances depends on the resident time of the catalyst in the re-generator, the concentration of oxygen and the temperature for the treatment. The treated catalyst containing carbonaceous substances in a reduced concentration is returned to the reactor 1 through a screw feeder 3.

In the step of Beckmann rearrangement, carbon and nitrogen components are deposited on the catalyst by polycondensation of cyclohexanone oxime or ε-caprolactam. By the treatment with the oxygen-containing gas in the regeneration step, removal of not only the deposited carbon but also the deposited nitrogen component is performed.

In the present inventors' studies, it has been revealed that an important relationship exists between the amount of the nitrogen component that remains on the catalyst and the performance of the catalyst, particularly in its selectivity to ε-caprolactam. Thus, the inventors have found that, when a catalyst having a lowered activity due to use thereof for a long time is re-generated with an oxygen-containing gas, a superior selectivity to ε-caprolactam is obtained by a catalyst having an appropriate amount of the nitrogen component remaining thereon rather than a catalyst in which carbon and nitrogen components are completely removed, for example, by combustion.

Specifically, by controlling the nitrogen content in the regenerated catalyst within a range of 10 ppm to 2,500 ppm, a desired continuous long term reaction can be conducted, while holding the selectivity at a higher level. The nitrogen content in the regenerated catalyst may be measured on its way to the reaction step from the re-generating step while the regenerated catalyst being returned to the reaction step. When the nitrogen content in the catalyst is lower than 10 ppm, the selectivity to ε-caprolactam is inferior, and when it is higher than 2,500 ppm, the conversion of cyclohexanone oxime is lowered.

The nitrogen content in the catalyst can be obtained by a method in which nitrogen oxides generated by oxidizing the catalyst with oxygen gas are measured with a gas chromatography apparatus or an infrared spectrophotometer.

The Beckmann rearrangement reaction is conducted in a fluidized bed system. The catalyst may be used in a shape of minute spherical particles having a diameter of 0.3 mm or below, which may be shaped by a method including spray drying or the like. In the rearrangement reaction, cyclohexane oxime may be fed at a ratio where the amount of fed cyclohexane oxime to that of the catalyst placed in the reactor (space velocity, WHSV) is about 0.5 to about 20 $h^{-1}$, preferably about 1 to about 10 $h^{-1}$.

The reaction temperature may be within the range of about 250° C. to about 500° C., and preferably is about 300° C. to about 450° C. The reaction pressure may be within the range of about 0.01 MP to about 0.5 MP, preferably about 0.02 MP to about 0.2 MP.

In the Beckmann rearrangement reaction, it is advantageous to allow a lower alcohol having 1 to 6 carbon atoms to co-exist with cyclohexanone oxime. Methanol and ethanol are particularly preferred alcohols. The amount of the alcohol allowed to co-exist is preferably within a range of about 0.1 to about 5 times the weight of cyclohexanone oxime.

It is also advantageous to allow water to co-exist together with cyclohexanone oxime. The amount of water allowed to co-exist is preferably 2.5 times the mole of cyclohexanone oxime or less.

In addition, an inert gas may be introduced to the reaction system. Examples of the inert gas include nitrogen, argon, carbon dioxide and the like.

The re-generation step of the catalyst is carried out in a fluidized bed system. The catalyst withdrawn from the reactor for Beckmann rearrangement is introduced into a re-generator and is treated with an oxygen-containing gas. As the oxygen-containing gas, air is preferably used and may be used if desired, after being mixed with an inert gas such as nitrogen or the like to give an oxygen concentration of 20% or less. The temperature for the treatment may be within the range of about 350° C. to about 700° C., preferably about 400° C. to about 550° C. When the temperature is lower than about 350° C., the carbonaceous substances deposited on the catalyst cannot be sufficiently removed and the remaining amount of nitrogen on the catalyst tends to be large and, therefore, the activity of the catalyst tends to be undesirably lowered. When the temperature is higher than about 700° C., the catalyst such as zeolite is liable to be decomposed and the activity of the catalyst tends to be gradually lowered.

The pressure for the re-generation treatment may be adopted within approximately the same range as that for Beckmann rearrangement. The residence time of the catalyst in the re-generation step may be about 0.5 hour to about 500 hours in average.

The amount of the catalyst to be sent from the reactor for Beckmann rearrangement to the re-generator may be about 0.1% by weight to about 75% by weight, preferably about 0.5% by weight to about 50% by weight, of the amount present in the reactor for Beckmann rearrangement per unit time.

ε-Caprolactam can be advantageously produced in the above described manner. According to the invention, ε-caprolactam can be steadily produced with a high yield for a long period. In addition, a continuous long-term operation can be carried out with a high conversion or a high selectivity.

The present invention will now be described in more detail by means of Examples, which should not be construed as a limitation upon the scope of the invention.

EXAMPLES

Example 1

Into a reactor 1 constituted of a straight stainless steel tube having a diameter of 80 mm and a length of 1,000 mm equipped with a freeboard part having a diameter of 200 mm and a length of 1,000 mm and into a stainless steel re-generator 2 having a diameter of 65 mm and a length of 2,000 mm, there was packed 250 g and 400 g, respectively, of a catalyst in the shape of fine powders having a diameter of 0.3 mm or less comprising a zeolite with a MFI structure as its principal component. (The reactor 1 and the re-generator 2 are set as illustrated in FIG. 1.) The particles of the catalyst in the reactor 1 were fluidized by introducing nitrogen gas through the pipe 9 into the reactor 1 at a rate of 0.4 m$^3$/hour. The temperature in the reactor was elevated to 350° C. On the other hand, the air was introduced through the pipe 7 into the re-generator 2 at a rate of 0.2 m$^3$/hour to fluidize the catalyst, which was heated to 500° C. while fluidizing. When both temperatures were stabilized, cyclohexanone oxime in the gaseous form was fed through the pipe 9 to the reactor 1 at a rate of 1,260 g/hour together with gaseous methanol at a rate of 2,240 g/hour. In addition, nitrogen gas was introduced from the pipe 5 at a rate of 1.0 m$^3$/hour.

By controlling the mouth openings of the control valve 4 and the screw feeder 3, the catalyst was circulated from the reactor 1 to the re-generator 2 and from the re-generator 2 to the reactor 1 at a rate of 20 g/hour. The product produced by the reaction was withdrawn through the pipe 6 to outside the system and was analyzed. After passage of 200 hours, the conversion of cyclohexanone oxime was 99.6% and the selectivity to ε-caprolactam was 95.7%. The nitrogen content of the catalyst going from the re-generator 2 to the reactor 1 was analyzed to be 110 ppm.

It is noted that the conversion of cyclohexanone oxime and the selectivity to ε-caprolactam were calculated based on the following formulae:

Conversion of cyclohexanone oxime (%)
=[1—(molar amount of unreacted cyclohexanone oxime)/(molar amount of cyclohexanone oxime fed in the reaction)]×100

Selectivity towards ε-caprolactam (%)
=[(molar amount of produced ε-caprolactam)/(molar amount of cyclohexanone oxime consumed in the reaction)]×100

Comparative Example 1

The reaction and the re-generation were carried out under the same conditions as those in Example 1 except that the rate of circulation of the catalyst was changed to 200 g/hour. After passage of 200 hours, the conversion of cyclohexanone oxime was 97.8% and the selectivity to ε-caprolactam was 94.7%. The nitrogen content of the catalyst going from the re-generator 2 to the reactor 1 was analyzed to be 3,100 ppm.

What is claimed is:

1. A process for producing ε-caprolactam which comprises the steps of (i) subjecting cyclohexanone oxime to a gaseous phase Beckmann rearrangement reaction in a fluidized bed system using a solid catalyst, excluding a boric acid catalyst, and (ii) re-generating the solid catalyst for use in step (i), wherein said step of re-generating the solid catalyst comprises the sub-steps of (a) continuously or intermittently withdrawing the solid catalyst from the Beckmann rearrangement reaction step (i), (b) treating the solid catalyst with an oxygen-containing gas at an elevated temperature so that the nitrogen content of the catalyst falls within a range of from 10 ppm to 2,500 ppm on its way to the reaction step from the re-generating step, and (c) returning the so treated solid catalyst to the Beckmann rearrangement reaction step (i).

2. The process for producing ε-caprolactam according to claim 1, wherein the solid catalyst is a pentasil-type zeolite.

3. The process for producing ε-caprolactam according to claim 2, wherein said zeolite has a MFI structure.

4. The process for producing ε-caprolactam according to claim 2, wherein said zeolite has a molecular skeleton that contains silicon as its principal component and another element M, wherein M is selected from Al, B, Ga, In, Ge, Fe, Ti, Zr and combinations thereof, and the atomic ratio Si/M of said zeolite is 50 or more.

5. The process for producing ε-caprolactam according to claim 2, wherein said atomic ratio Si/M is 500 or more.

6. The process for producing ε-caprolactam according to claim 1 or 2, wherein said Beckmann rearrangement reaction is carried out in the co-existence of at least one lower alcohol having 1 to 6 carbon atoms.

* * * * *